United States Patent [19]

Brittain et al.

[11] Patent Number: 4,478,847
[45] Date of Patent: Oct. 23, 1984

[54] 1'-SUBSTITUTED-SPIRO[PYRROLIDINE-3,3'-INDOLINE]-2,2',5-TRIONES

[75] Inventors: David R. Brittain, Macclesfield; Robin Wood, Hazel Grove, both of England

[73] Assignee: Imperial Chemical Industries PLC, London, England

[21] Appl. No.: 377,135

[22] Filed: May 11, 1982

[30] Foreign Application Priority Data

May 12, 1981 [GB] United Kingdom ............... 8114397

[51] Int. Cl.³ .................... A61K 31/40; C07D 209/96
[52] U.S. Cl. ..................................... 424/274; 548/410
[58] Field of Search ..................... 548/410; 424/274

[56] References Cited

U.S. PATENT DOCUMENTS 4,177,230  9/1978  Sarges ............................... 424/273
4,307,108 12/1981  Belletire ............................ 424/274

OTHER PUBLICATIONS

H. Schaefer, Archiv. der Pharmazie, (Weinheim), 1970, 303, 183–191; Chem. Abstracts, 1970, 73, 3739.

Primary Examiner—Donald G. Daus
Assistant Examiner—M. C. Eakin
Attorney, Agent, or Firm—Cushman, Darby & Cushman

[57] ABSTRACT

The invention provides a pharmaceutical composition comprising an aldose reductase inhibitory 1'-substituted-spiro[pyrrolidine-3,3'-indoline]-2,2',5-trione of the formula:

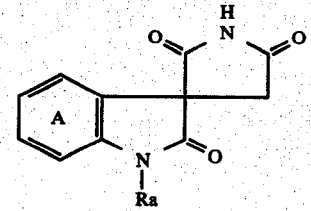

wherein Ra is (2-7C)alkyl or (3-7C)alkenyl, naphthylmethyl or cinnamyl optionally bearing one or two halogeno nuclear substituents, or Ra is benzyl optionally bearing one or two substituents and benzene ring A optionally bears one or two substituents, trifluoromethyl and nitro; or a salt thereof with a base affording a pharmaceutically acceptable cation; or a non-toxic, biodegradable precursor thereof; together with a pharmaceutically acceptable diluent or carrier. The invention also provides novel compounds of formula I and processes for their manufacture.

The compositions are of application in the treatment or prophylaxis of the side effects of diabetes or galactosemia.

9 Claims, No Drawings

1'-SUBSTITUTED-SPIRO[PYRROLIDINE-3,3'-INDOLINE]-2,2',5-TRIONES

This invention relates to novel pharmaceutical compositions which contain as active ingredient a cyclic imide having the property of inhibiting the enzyme aldose reductase in vivo. More particularly, the cyclic imide is a 1'-substituted spiro[pyrrolidine-3,3'-indoline]-2,2',5-trione and the compositions are in general useful in the treatment or prophylaxis of those complications of protracted diabetes or galactosemia which are due at least in part to the undesirable tissue accumulation of sorbitol or galactitol, respectively.

The enzyme aldose reductase is responsible in man and other warm-blooded animals for the catalytic conversion of aldoses, for example glucose and galactose, to the corresponding alditols, for example sorbitol and galactitol respectively. Alditols penetrate cell membranes poorly and, once formed, tend to be removed only by further metabolism. As a consequence, alditols tend to accumulate within cells where they are formed, for example in the lens, peripheral nerve tissue and kidney, causing a rise in internal osmotic pressure which may in turn be sufficient to destroy or impair the function of the cells themselves. In addition, raised alditol levels may result in abnormal levels of their metabolites which may themselves impair or damage cellular function. However, the enzyme aldose reductase has a relatively low substrate affinity, that is, it is only effective in the presence of relatively large concentrations of aldose. Such large concentrations of aldose are present in the clinical conditions of diabetes (excessive glucose) and galactosemia (excessive galactose). As a consequence, inhibitors of the enzyme aldose reductase are useful in the reduction or prevention of the development of those complications of protracted diabetes or galactosemia which may be due in part to the accumulation of sorbitol or galactitol respectively. Such complications are, for example, macular oedema, cataract, retinopathy, nephropathy or impaired neural conduction.

It is known that certain spiro-linked hydantoins (spiro-linked imidazolidine-2,5-diones) derived from various bicyclic ketones are inhibitors of the enzyme aldose reductase, for example the compounds of the general formula:

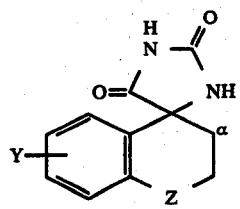

wherein Z is oxygen, sulphur, sulphinyl, sulphonyl, methylene or a direct bond, and Y stands for various optional substituents described by Sarges in U.S. Pat. Ser. No. 4,117,230. We have now discovered that certain spiro-linked succinimides (spiro-linked pyrrolidine-2,5-diones) of formula I below and which are derived from indoline-2,3-diones possess potent aldose reductase inhibitory properties, and this is the basis for our invention. This discovery is particularly surprising in view of the various chemical differences involved, for example the replacement of the imidazolidine imino moiety (which is adjacent to the spiro-carbon) by methylene, and the introduction of an N-substituted iminocarbonyl (NRa.CO) group in the α-position of the saturated ring, which position has hitherto only been occupied by methylene.

Certain of the spiro-linked succinimides of formula I are known [H. Schaefer, *Archiv der pharmazie* (Weinheim), 1970, 303, 183–191; *Chem.Abs.*, 1970, 73, 3739] but have not hitherto been known to possess aldose reductase inhibitory properties.

According to the invention there is provided a pharmaceutical composition comprising as active ingredient a 1'-substituted-spiro[pyrrolidine-3,3'-indoline]-2,2', 5-trione of the formula:

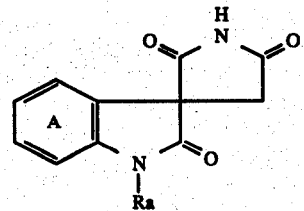

wherein Ra is (2-7C)alkyl or (3-7C)alkenyl, naphthylmethyl or cinnamyl optionally bearing one or two halogeno nuclear substituents, or Ra is benzyl optionally bearing one or two substituents independently selected from halogeno, (1-4C)alkyl, (1-4C)alkoxy, cyano, nitro and trifluoromethyl, located in the 2, 3, 4 or 5 position; and benzene ring A optionally bears one or two substituents independently selected from halogeno, (1-4C)alkyl, trifluoromethyl and nitro; or a salt thereof with a base affording a pharmaceutically acceptable cation; or a non-toxic, biodegradable precursor thereof; together with a pharmaceutically acceptable diluent or carrier.

The compounds of formula I are derivatives of spiro[pyrrolidine-3,3'-indoline]-2,2',5-trione which will be numbered throughout this specification as follows:

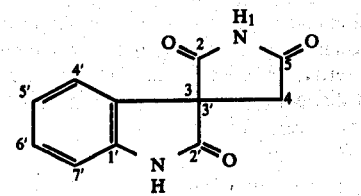

Throughout this specification the terms Ra, Rb et cetera are used to signify generic radicals and have no other significance.

The compounds of formula I all possess at least one asymmetric carbon atom, namely the spiro carbon atom at position 3 of the pyrrolidine ring. The compounds of formula I therefore exist, and may be isolated, in one or more racemic and optically active forms. This invention encompasses the compounds of formula I in racemic form or in any optically-active form which possesses aldose reductase inhibitory properties, it being well known in the art how to prepare optically active forms by resolution of the racemic form, or by synthesis from optically-active starting materials, and how to determine the aldose reductase inhibitory properties by the standard tests described hereinbelow.

The compositions of the invention may be in a form suitable for oral administration, for example in the form of a tablet, capsule, granule, dispersible powder, syrup, elixir, emulsion, suspension or gel; for parenteral administration, for example in the form of a sterile injectable aqueous suspension or solution, or oily solution or suspension; for rectal administration, for example in the form of a suppository ; or for topical administration to the eye, for example in the form of an ointment, gel or sterile solution buffered at an ophthalmically acceptable pH, for example in the range pH 7.0–7.6.

The compositions may be manufactured by normal techniques of pharmacy using procedures, carriers and diluents well known in the art. In general oral compositions are preferred, but the exact form of composition and route of administration may vary depending on the host and aldose reductase containing tissue under treatment. Tablets may contain in addition to a compound of formula I or a salt thereof (hereinafter referred to as the active ingredient) one or more inert diluents and compression aids, for example lactose, magnesium carbonate or calcium phosphate; granulating and disintegrating agents, for example sodium or calcium carboxymethylcellulose, microcrystalline cellulose or maize starch; binding agents, for example polyvinylpyrrolidone or gelatine; wetting agents, for example sodium lauryl sulphate or polysorbate; and lubricating agents, for example magnesium stearate. Tablets may be uncoated or they may be coated by known techniques to increase stability, to mask unpalatable taste, or to delay release of the active ingredient. They may in addition contain one or more sweetening, flavouring and colouring agents.

Capsules may be of hard gelatine and may contain the active ingredient alone, or in admixture with one or more solid non-toxic diluents or agents such as those mentioned above. Alternatively, capsules may be of soft gelatine wherein the active ingredient is mixed with an oily medium.

Syrups and elixirs are formulated with sweetening agents, for example sucrose or saccharin, and may also contain one or more conventional demulcents, flavouring and colouring agents.

Emulsions and suspensions may contain one or more conventional suspending agents, for example sodium carboxymethylcellulose or aluminium magnesium silicate, and dispersing and wetting agents, for example, a polysorbate, together with one or more conventional diluents, for example water, ethanol, glycerol, propylene glycol, polyethylene glycol, or an edible vegetable or mineral oil.

Gels may contain one or more conventional gelling agents, for example animal and vegetable fats, waxes, cellulose derivatives, silicones or polyethylene glycols.

Dispersible powders and granules which are suitable for the extemporaneous preparation of an aqueous suspension or solution may contain one or more conventional dispersing, suspending or wetting agents, buffering agents, or preservatives.

Compositions intended for parenteral or topical administration to the eye may be sterilised by conventional procedures.

Solutions for topical administration to the eye, for example in the treatment of diabetic cataracts, may contain one or more conventional buffers, for example boric acid, sodium or potassium carbonate, bicarbonate, acetate or borate; gelling or thickening agents, for example dextran, glycerol, cellulose derivatives or polyethylene glycol; or other conventional excipients well known in the art for use in the preparation of ophthalmic compositions. Similarly, ointments for topical administration to the eye may contain conventional excipients such as soft paraffin together with emulsifying and or thickening agents such as sorbitan monostearate.

Suppositories for administration of the active ingredient per rectum may be prepared by mixing the active ingredient with one or more conventional non-irritant excipients which are solid at ordinary temperatures but liquid at rectal temperature and which will thus melt in the body, releasing the active ingredient.

All the pharmaceutical compositions may be conveniently formulated together with a conventional antioxidant, for example sodium metabisulphite, and/or a preservative, for example methyl or propyl p-hydroxybenzoate.

Dosage unit forms of a composition of the invention, for example tablets, capsules or suppositories will in general contain 10–500 mg. of active ingredient, depending on the form involved.

Solutions and ointments for topical administration to the eye will in general contain 0.02–2.0% by weight of active ingredient.

A particular value for Ra when it is (2-7C)-alkyl is, for example, ethyl, propyl, butyl, pentyl, hexyl or heptyl. A particular value for Ra when it is (3-7C)alkenyl is, for example, allyl, 2-methylallyl or 3-butanol.

A particular value for Ra when it is naphthylmethyl or cinnamyl bearing one or two halogeno nuclear substituents is, for example, 5-chloro-1-naphthylmethyl, 6-chloro-2-naphthylmethyl, 4-chlorocinnamyl or 3,4-dichlorocinnamyl.

Particular values for substituents which may be present on benzene ring A or nuclear substituents as part of Ra are, by way of example:

for halogeno; fluoro, chloro, bromo or iodo;
for (1-4C)alkyl; methyl or ethyl; and
for (1-4C)alkoxy; methoxy or ethoxy.

The term non-toxic, biodegradable precursor includes derivatives of the compounds of formula I defined above in which the imino hydrogen atom in the pyrrolidine ring is replaced by a biodegradable protecting group known in the art, which group is, not inherently toxic and which is capable of removal in vivo (for example by enzymic hydrolysis) to liberate the compound of formula I in sufficient quantity to inhibit the enzyme aldose reductase and without giving rise to pharmacologically unacceptable by-products. Examples of suitable groups for inclusion in biodegradable precursors of compounds of formula I include alkoxycarbonyl, aralkoxycarbonyl, alkoxyoxalyl and 1-(alkoxycarbonyloxy)alkyl groups, such as ethoxycarbonyl, t-butyloxycarbonyl, benzyloxycarbonyl, ethoxyoxalyl, methoxyoxalyl and pivaloyloxymethyl groups. The biodegradable precursors are not in general themselves inhibitors of the enzyme aldose reductase, but are active in vivo by virtue of removal of the biodegradable protecting radical. It will be apparent therefore that by suitable choice of biodegradable protecting groups (for example based on their generally known rates of enzymic degradation) it is possible to produce biodegradable precursors of compounds of formula I whose bioabsorption and distribution properties differ from those of the compounds of formula I.

Specific values for benzene ring A of particular interest are, for example, when it is unsubstituted or bears a fluoro, chloro, bromo, methyl or trifluoromethyl substituent located in the 5'-, 6'-, or 7'-position, and especially a 5'-fluoro, 5'-chloro, 5'-bromo, 6'-fluoro, 6'-chloro, 6'-methyl, 7'-fluoro, 7'-chloro, 7'-methyl or 7'-trifluoromethyl substituent.

Specific values for Ra of particular interest are, for example, when it is propyl, butyl, pentyl, hexyl or heptyl, 1-naphthylmethyl, 2-naphthylmethyl, cinnamyl, halogenocinnamyl (especially 4-chlorocinnamyl), dihalogenocinnamyl (especially 3,4-dichlorocinnamyl), benzyl, (1-4C)alkylbenzyl (especially 4-methylbenzyl), halogeno- or (trifluoromethyl)-benzyl [especially 4-chlorobenzyl, 4-bromobenzyl, (3-trifluroomethyl)-benzyl or (4-trifluoromethyl)benzyl],or dihalogenobenzyl (especially 2,4-dichlorobenzyl, 4-chloro-2-fluorobenzyl, 4-bromo-2-fluorobenzyl, 2-fluoro-4-iodobenzyl, 3,4-dichlorobenzyl, 3-bromo-4-chlorobenzyl or 4-bromo-3-chlorobenzyl).

In general, when Ra is alkyl or alkenyl it is preferred that benzene ring A bears at least one substituent and preferably at least one halogeno substituent.

Specific groups of novel compounds of formula I which are of special interest are mentioned hereinafter. However, of the known compounds described by Schaefer (see above), the compounds 1'-(4-chlorobenzyl)-spiro [pyrrolidine-3,3'-indoline]-2,2', 5-trione and 1'-(3,4-dimethoxybenzyl)-spiro[pyrrolidine-3,3'-indoline]-2,2',5-trione, or salts thereof, are of particular interest as active ingredients of compositions according to the invention.

Particular salts of compounds of formula I with bases affording a pharmaceutically acceptable cation are, for example, alkali metal or alkaline earth metal salts, such as sodium, potassium, calcium or magnesium salts, aluminium or ammonium salts or salts with organic bases such as triethanolamine.

The invention also provides a novel 1'-substituted-spiro[pyrrolidine-3,3'-indoline]-2,2',5-trione of the formula:

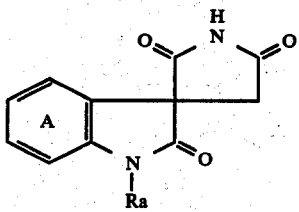

I wherein Ra is (2-7C)alkyl or (3-7C)alkenyl, naphthylmethyl or cinnamyl optionally bearing one or two halogeno nuclear substituents, or Ra is benzyl optionally bearing one or two substituents independently selected from halogeno, (1-4C)alkyl, (1-4C)alkoxy, cyano, nitro and trifluoromethyl, located in the 2, 3, 4 or 5 position; and benzene ring A optionally bears one or two substituents independently selected from halogeno, (1-4C)alkyl, trifluoromethyl and nitro; or a salt thereof with a base affording a pharmaceutically acceptable cation; or a nontoxic biodegradable precursor thereof; but excluding those compounds of formula I wherein Ra is benzyl, 4chlorobenzyl or 3,4-dimethoxybenzyl and benzene ring A is unsubstituted, and 1'-benzyl-5'-chloro-spiro[pyrrolidine-3,3'-indoline]2,2',5-trione.

Particular values for Ra and benzene ring A are defined hereinbefore.

Specific groups of novel compounds of the invention are comprised by the following:

(i) Ra has any of the meanings defined above; and benzene ring A is substituted as defined above apart from by a 5-chloro substituent;

(ii) Ra is (2-7C)alkyl especially propyl, butyl, pentyl or hexyl or (3-7C)alkenyl especially allyl or 3-butenyl, naphthylmethyl or cinnamyl optionally bearing one or two halogeno nuclear substituents, or a benzyl radical bearing one or two substituents as defined above; and benzene ring A bears a 5-chloro substituent;

(iii) Ra has any of the meanings defined above apart from 4-chlorobenzyl or 3,4-dimethoxybenzyl; and benzene ring A is unsubstituted;

(iv) Ra is (2-7C)alkyl or (3-7C)alkenyl; and benzene ring A has any of the meanings defined above;

(v) Ra is naphthylmethyl or cinnamyl optionally bearing one or two halogeno substituents; and benzene ring A has any of the meanings defined above; or (vi) Ra has any of the meanings defined above; and benzene ring A bears a 5'-fluoro, 5'-bromo, 6'-halogeno (especially 6'-fluoro or 6'-chloro), 6'-(1-4C)alkyl (especially 6'-methyl) 7'-halogeno (especially 7'-fluoro or 7'-chloro), 7'-(1-4C)alkyl (especially 7'-methyl), or 7'-trifluoromethyl substituent;

together with in each group the salts thereof with bases affording a pharmaceutically acceptable cation, and the non-toxic biodegradable precursors thereof.

A preferred group of novel compounds of the invention comprises those compounds of formula I wherein Ra is benzyl as defined above bearing at least one halogeno or trifluoromethyl substituent, and benzene ring A optionally bears one or two substituents as defined above located at the 5', 6' or 7' position; together with the salts thereof, and the non-toxic biodegradable precursors thereof; but excluding 1'-(4-chlorobenzyl)-spiro[pyrrolidine-3;3'-indoline]-2,2',5-trione.

A second preferred group comprises those compounds of formula I wherein Ra is benzyl bearing two independently selected halogeno substituents located at fluoro, 4-bromo-2-fluoro, 2-fluoro-4-iodo, 2,4-dichloro-3,4-dichloro, 4-bromo-3-chloro and 3-bromo-4-chloro substituents), or Ra is benzyl bearing bromo or trifluoromethyl located at positions 3 or 4; and benzene ring A has any of the meanings defined immediately above in the first preferred group; together with the salts thereof, and the non-toxic biodegradable precursors thereof.

Specific novel compounds of formula I are provided in the accompanying Examples. However, compounds of particular interest are, for example:

| Ra | Benzene ring A substituent |
|---|---|
| 3,4-dichlorobenzyl | unsubstituted |
| 2-fluoro-4-iodobenzyl | unsubstituted |
| 4-bromo-2-fluorobenzyl | unsubstituted |
| 4-bromo-2-fluorobenzyl | 5'-chloro |
| 3,4-dichlorobenzyl | 5'-chloro |
| 3,4-dichlorobenzyl | 5'-fluoro |
| 3,4-dichlorobenzyl | 7'-fluoro |
| 4-bromo-2-fluorobenzyl | 7'-fluoro |
| 4-bromo-2-fluorobenzyl | 7'-methyl |
| 2-fluoro-4-iodobenzyl | 7'-fluoro | together with the salts thereof, and non-toxic, biodegradable precursors thereof.

A preferred non-toxic, biodegradable precursor is, for example, pivaloyloxymethyl.

The novel compounds of formula I may be obtained by any process known in the art for the manufacture of structurally analogous compounds. Such processes are provided as a further feature of the invention and are illustrated by the following procedures in which, unless otherwise stated, Ra and benzene ring A have any of the above mentioned values and are subject to the aforementioned disclaimers:

(a) Decarboxylating an acid of the formula:

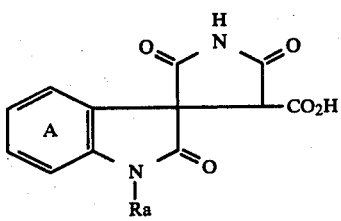

under the influence of heat.

The decarboxylation may be carried out at a temperature in the range, for example, 60°–200° C. and a suitable solvent or diluent, for example acetic acid diethanolamine or quinoline (optionally together with copper powder) may conveniently be present.

The starting materials of formula II are conveniently generated in situ by hydrolysis of the corresponding derivative of the formula:

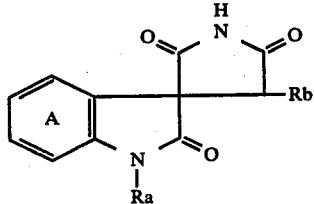

wherein Rb is alkoxycarbonyl (such as methoxycarbonyl, ethoxycarbonyl or t-butoxycarbonyl), aralkoxycarbonyl (such as benzyloxycarbonyl), cyano or carbamoyl. The hydrolysis may be carried out using conventional acid or base catalysed conditions, for example as illustrated in the accompanying Examples, and at a temperature in the range, for example, 40°–100° C. When base catalysis is used the acid of formula II must be generated from the salt first obtained, by acidification with a mineral acid such as hydrochloric acid. When acid catalysis is used, the acid of formula II may undergo spontaneous decarboxylation to generate the compound of formula I.

When Rb is an (α,α-dibranched)alkoxycarbonyl group, such as t-butoxycarbonyl, the acid of formula II may be generated by thermolysis at a temperature in the range, for example, 120°–180° C., preferably in the absence of solvent or diluent and under reduced pressure. Under these conditions the acid of formula II undergoes decarboxylation to the compound of formula I.

When Rb is an aralkoxycarbonyl group, such as benzyloxycarbonyl, the acid of formula II may also be formed by conventional hydrogenolysis, for example using hydrogen at atmospheric pressure in a solvent, such as ethanol or aqueous ethanol, using a palladium based catalyst.

Particularly convenient conditions for the in situ formation and subsequent decarboxylation of an acid of formula II are provided by heating a derivative of formula III defined above in a (2-6C)alkanoic acid; such as acetic or propionic acid, in the presence of an inorganic acid, such as hydrogen chloride or hydrogen bromide, and at a temperature in the range for example, 100°–150° C. This process is included on a further feature of the invention.

The starting materials of formula III may be obtained by cyclisation of a bifunctional derivative of the formula:

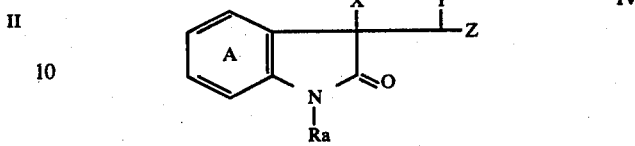

wherein one of X, Y and Z is cyano or carbamoyl and the other two are independently selected from cyano, carbamoyl, alkoxycarbonyl (such as methoxycarbonyl or ethoxycarbonyl) and aralkoxycarbonyl (such as benzyloxycarbonyl). A preferred value for X and Y is, for example, cyano and for Z is, for example, methoxycarbonyl or ethoxycarbonyl.

This process is normally performed in the presence of an acid or base catalyst, preferably in the presence of an inorganic acid catalyst such as a hydrogen halide, sulphuric acid or polyphosphoric acid. The process is conveniently performed in a suitable solvent or diluent, for example a (1-6C)-alkanol (such as methanol or ethanol) or a (2-6C)-alkanoic acid (such as acetic or propionic acid) and is normally carried out at a temperature in the range, for example 20° to 120° C. If somewhat higher temperatures are employed, it is possible to carry out the conversion to, and decarboxylation of, the acid of formula II in situ, for example by using hydrogen bromide in acetic acid at the boiling point of the reaction mixture.

The starting materials of formula IV may be obtained by conventional procedures of organic chemistry well known in the art. Thus, those compounds of formula IV wherein X is cyano may be obtained by addition of cyanide to an unsaturated compound of the formula:

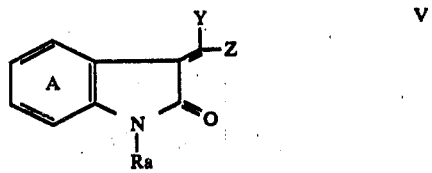

or a geometric isomer thereof, wherein Y and Z have the meanings defined above, for example by reacting a compound of formula V with potassium cyanide in methanol at a temperature in the general range 10° to 50° C.

The starting materials of formula V are themselves obtained from the corresponding 1-substituted-indoline-2,3-diones of the formula:

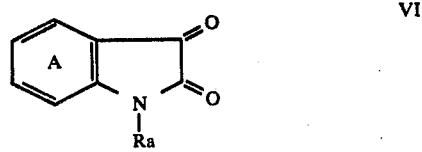

by condensation with a compound of the formula Y.CH₂.Z, wherein Y and Z have the meanings defined above, preferably in the presence of a base catalyst such as piperidine or morpholine, in a suitable solvent such as methanol or ethanol, and at a temperature in the general range 10° to 100° C.

The compounds of formula Y.CH$_2$.Z and VI are in general well known in the art or may be obtained by conventional procedures, such as those illustrated in the accompanying Examples.

(b) Deprotecting a compound of the formula:

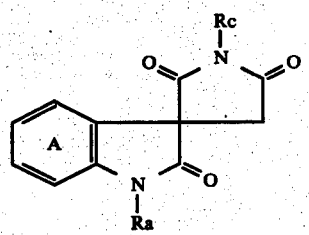

VII wherein Rc is a protecting group, for example formyl, (2-6C)alkanoyl, benzoyl, [(1-6C)alkoxy]carbonyl, benzyloxycarbonyl, benzylhydryl, triphenylmethyl(trityl) or tri-[(1-4C)alkyl]silyl, in particular formyl, acetyl, benzoyl, methoxycarbonyl, t-butoxycarbonyl, benzyloxycarbonyl, benzylhydryl, triphenylmethyl or trimethylsilyl.

It will be appreciated that, depending on the nature of the group Rc, different deprotection methods are involved. Thus, when Rc is benzylhydryl, trityl or benzyloxycarbonyl, reductive deprotection may be employed, for example using hydrogenation at or near atmospheric pressure in the presence of a suitable catalyst, such as palladium on an inert support, at a temperature in the range, for example 10° to 40° C. Also, when Rc is an acyl group, conventional acid or base catalysed hydrolysis may be used to carry out the deprotection, for example by reaction with a hydrogen halide in aqueous ethanol or acetic acid, or with aqueous ethanolic sodium hydroxide or potassium hydroxide, at a temperature in the range 20° to 60° C. Further, when Rc is a t-butoxycarbonyl or trimethylsilyl radical, the deprotection may be carried out at a temperature in the range, for example, 10° to 40° C. using a strong acid such as hydrochloric or trifluoroacetic acid, optionally in the presence of an inert diluent or solvent.

The starting materials of formula VII may be obtained, for example, by reacting a compound of the formula:

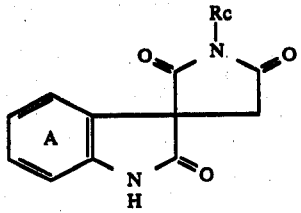

VIII with a halogeno compound of the formula Ra.Hal wherein Hal is halogeno, especially chloro, bromo or iodo, in the presence of a base.

A suitable base is, for example, sodium or potassium hydride or carbonate and a convenient solvent or diluent which may be used is, for example, N,N-dimethylformamide or dimethyl sulphoxide. In general, the compound of formula VIII will be reacted with the base before the addition of the compound of the formula Ra.Hal. and the reaction will be carried out at a temperature in the range, for example 10° to 60° C.

The starting materials of formula VIII may be obtained by alkylation of a salt of the formula:

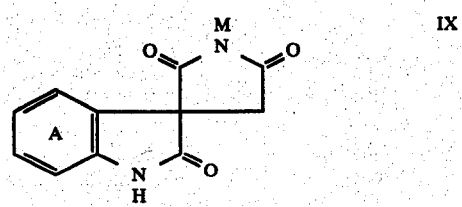

IX wherein M is an alkali metal cation, such as lithium, sodium or potassium, formed in situ by addition of one molecular equivalent of a suitable base, such as butyl lithium, sodium hydride or potassium hydride, to a solution of the compound of formula IX (M=H) in a suitable polar solvent such as N,N-dimethylformamide, dimethyl sulphoxide, tetrahydrofuran, hexamethylphosphoramide or N-methyl-2-pyrrolidone, diluted if necessary with an inert diluent. The alkylating agent will generally be a compound of the formula Rc.Hal as defined above and the salt of formula IX will ordinarily be added dropwise in solution to a solution of the alkylating agent in the reaction solvent, generally at a temperature in the range, for example −10° to 50° C., in order to minimise the possibility of alkylation at the indoline nitrogen atom.

The starting materials of formula IX (M=H) may be obtained by an analogous procedure to that in process (a) hereinabove but starting from the appropriate 1-unsubstituted indoline-2,3-dione (isatin) derivative.

(c) Alkylating a salt of the formula:

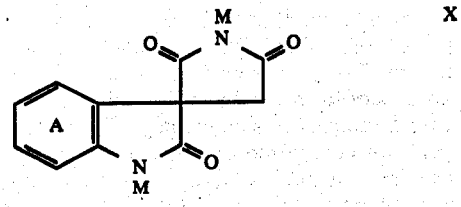

X wherein M is an alkali metal cation as defined above, by reaction with an alkylating agent of the formula Ra.Q, wherein Q is a suitable leaving group such as halogeno (especially chloro, bromo or iodo, (1-6C)-alkylsulphonyloxy (especially methylsulphonyloxy) or arylsulphonyloxy (especially 4-methylphenylsulphonyloxy).

The salt is preferably formed in situ by reaction of a compound of formula X (M=H) with at least two molecular equivalents of base, for example an alkali metal hydride or hydroxide such as sodium or potassium hydride, or sodium or potassium hydroxide. The process is preferably carried out in a suitable polar solvent, for example a (1-4C)alkanol (such as methanol or ethanol), N,N-dimethylformamide or dimethyl sulphoxide, optionally together with a suitable inert diluent, and at a temperature in the range, for example, 10° to 100° C. It is generally preferred to use only a slight excess of the alkylating agent and to add it dropwise to the reaction mixture in order to minimise the possibility of dialkylation occurring. The starting material of formula X (M=H) in the above process can be obtained by an analogous procedure to process (a) starting from the appropriate 1-unsubstituted-indoline-2,3-dione (isatin)-derivative.

(d) For a compound of formula I wherein benzene ring A bears a nitro substituent and/or Ra is benzyl bearing a nitro substituent, nitrating the corresponding compound of formula I in which benzene ring A is unsubstituted or monosubstituted and/or Ra is unsubstituted benzyl or monosubstituted benzyl.

The nitration may be carried out under conventional procedures, for example in the presence of sulphuric acid, using nitric acid at a temperature in the range, for example, 0° to 30° C., or using fuming nitric acid at a temperature in the range, for example −20° to 10° C.

(e) For a compound of formula I wherein benzene ring A bears a chloro or bromo substituent, chlorinating or brominating the corresponding compound of formula I wherein benzene ring A is unsubstituted or monosubstituted.

The chlorination or bromination may be carried out using conventional procedures, for example using elemental chlorine or bromine, optionally in the presence of a Friedel-Craft's catalyst, such as ferric chloride, ferric bromide or iron powder, at a temperature in the range, for example 10° to 100° C. and in a suitable solvent or diluent, for example chloroform, nitrobenzene or acetic acid.

Alternatively, the chlorination or bromination may be carried out using sulphuryl chloride or bromide, optionally in the presence of iodine as catalyst at a temperature in the range, for example 10° to 100° C., and in a suitable solvent or diluent, for example acetic acid or chloroform.

Processes (d) and (e) are particularly suitable for the production of those compounds of formula I in which benzene ring A bears a 5-substituent using a compound in which benzene ring A is unsubstituted as starting material.

The non-toxic, biodegradable precursors of the compounds of formula I may be obtained by known acylation or alkylation procedures already used for the introduction of the necessary biodegradable protecting radicals. Examples of suitable acylating or alkylating reagents for incorporating a range of such protecting radicals are, for example, alkoxycarbonyl, aralkoxycarbonyl, alkoxyoxalyl and 1-(alkoxycarbonyloxy)alkyl halides, such as ethoxycarbonyl, t-butyloxycarbonyl, benzyloxycarbonyl, ethoxyoxalyl, methoxyoxalyl and pivaloyloxymethyl chloride.

The reaction may be performed under conventional N-acylation/alkylation conditions, for example in the presence of a base such as potassium carbonate or using the lithium, sodium or potassium salt of the compound of formula I, and in a suitable solvent or diluent, for example 1,2-dimethoxyethane, di-n-butyl ether or diethyl ether, at a temperature in the range, for example 10°–80° C.

The intermediates of formula III are novel and in many cases (for example when Rb=CN and Ra is halogenobenzyl) possess aldose reductase inhibitory properties in their own right. These novel intermediates of formula III and processes for their production as defined hereinabove are therefore provided as a further feature of the invention. The novel intermediates of formula V and processes for their production as defined hereinbefore are also provided as a further feature of the invention.

Whereafter, when a pharmaceutically acceptable salt is required, a compound of formula I in free base form is reacted with a base affording a pharmaceutically acceptable cation, using a conventional procedure well known in the art.

Further, when an optically active form of a compound of formula I is required, a racemic form of the said compound may be reacted with an optically-active form of a suitable organic base, for example brucine, coniine, 2-pipecoline or an N,N,N-trialkyl(1-phenylethyl)ammonium hydroxide such as N,N,N-trimethyl-(1-phenylethyl)ammonium hydroxide followed by conventional separation of the diastereoisomeric mixture of salts or complexes thus obtained, for example by fractional crystallisation from a suitable solvent, for example a (1-4C)alkanol, whereafter the optically-active form of the said compound may be liberated by treatment with acid using a conventional procedure, for example using an aqueous mineral acid, such as dilute hydrochloric acid.

The property of inhibiting the enzyme aldose reductase may be demonstrated in the following standard laboratory test. Thus, rats are made diabetic (as evidenced by severe glucosuria being present) by dosing with streptozotocin. The animals are then dosed daily with the test compound for 5 days. The animals are then killed and the eye lenses and sciatic nerves are removed. After a standard work-up procedure the residual sorbitol levels in each tissue are determined by gas liquid chromatography after conversion to the poly-trimethylsilyl derivatives. Inhibition of aldose reductase in vivo is then assessed by comparing the residual sorbitol levels in tissues from the dosed diabetic group of rats with those of an undosed group of diabetic rats and an undosed, normal group of rats.

Alternatively, a modified test may be used in which the streptozotocin induced diabetic rats are dosed daily with test compound for two days. After 2–4 hours from the final dose the animals are killed and the sciatic nerves are removed and assessed for residual sorbitol levels as described above.

In general the compounds of formula I produce significant inhibition of the enzyme aldose reductase (as measured by the effects on residual sorbitol levels) in either of the above tests at an oral dose of 100 mg./kg. or much less without any signs of overt toxicity or other untoward effects at the active dose or several multiples thereof. By way of illustration, the novel compound 1'-(3,4-dichlorobenzyl)spiro[pyrrolidine-3,3'-indoline]-2,2',5-trione produced a residual sorbitol level in the sciatic nerve which is approximately 20% of that obtained in control, undosed diabetic rats, following oral dosing at 50 mg./kg. for 2 days.

However, preferred compounds of formula I, such as those defined hereinbefore, in general reduce the residual sorbitol level in the sciatic nerve to that in normal undosed rats when administered at an oral dose in the range 5 to 30 mg./kg.

The property of inhibiting the enzyme aldose reductase may also be demonstrated in vitro. Thus, purified aldose reductase is isolated in known manner from bovine lenses. The percentage inhibition of this enzyme's ability in vitro to reduce aldoses to polyhydric alcohols, and particularly to reduce glucose to sorbitol, caused by a test compound is then determined using standard spectrophotometric methods. In this test the compounds of formula I in general show significant inhibition of the enzyme aldose reductase at a concentration of about $10^{-6}$M or much less. Compounds of formula I possessing potent inhibitory properties in this in vitro test and yet not particularly active by oral administration in the above in vivo tests may nevertheless be applied in an in vivo therapeutic or prophylactic situation, for example by topical administration direct to the tissue or organ in which inhibition of the enzyme is required, for example by topical administration to the eye.

However, the compounds of formula I will primarily be administered systemically (preferably by mouth) to a warm-blooded animal to produce an inhibitory effect on the enzyme aldose reductase, for example at a daily dose of 0.5 to 25 mg./kg. In man it is envisaged that a total daily dose in the range 10 to 750 mg. per man will be administered, if necessary, given in divided doses.

Topical formulations may be administered to the eye of an animal, for example man or dogs, requiring treatment for diabetic cataracts or retinopathy in a conventional manner, for example using a drop or eyewash topical formulation.

The invention also provides a method for inhibiting aldose reductase in a warm-blooded animal requiring such treatment which method comprises administering to said animal an aldose reductase inhibitory amount of a compound of formula I as defined anywhere hereinbefore, or a pharmaceutically acceptable salt thereof.

The compositions of the invention may also contain one or more other agents which may or are known to have a useful effect in the treatment of diabetes or galactosemia, for example a hypoglycaemic agent as tolbutamide, chlorpropamide, or glybenclamide.

The invention will now be illustrated by the following non-limiting Examples in which, unless otherwise stated:

(i) all evaporations were carried out by rotary evaporation in vacuo:

(ii) all operations were carried out at room temperature, that is in the range 18°–26° C.;

(iii) petroleum ether (b.p. 60°–80° C) is referred to as "petrol 60–80", and other petroleum ether fractions accordingly;

(iv) yields (where given) are for illustration only and are not necessarily the maximum attainable from the process in question;

(v) chromatography was carried out on silica gel (Art. No. 7734, available from E Merck, Darmstadt, West Germany) using conventional procedures; and (vi) all the final products of formula I were of satisfactory purity as indicated by TLC, NMR spectroscopy mass spectroscopy and/or microanalysis:

EXAMPLE 1

(All parts by weight)

A mixture of 1'-(4-chlorobenzyl)-spiro[pyrrolidine-3,3'-indoline]-2,2'5-trione (50 parts), lactose (27 parts) and maize starch (20 parts), was stirred thoroughly and a paste formed from maize starch (2 parts) and water (40 parts) was added and thoroughly mixed in. The resultant mass was passed through a 16 mesh screen, then dried at 60° C. and passed through a 20 mesh screen. Magnesium stearate (1 part) was added to the granules obtained, and the whole compressed by conventional means into tablets, containing 10, 20, 50 and 100 mg. of active ingredient and suitable for oral administration for therapeutic purposes.

Using a similar procedure, but replacing the active ingredient by any other compound of formula I or a salt thereof, for example a known compound as described hereinbefore or a novel compound as described hereinafter, tablets containing 10, 20, 50 and 100 mg. of active ingredient may be obtained.

EXAMPLE 2

(All parts by weight)

A mixture of 1'-(4-chlorobenzyl)-spiro[pyrrolidine-3,3'-indoline]-2,2',5-trione (50 parts), calcium carbonate (20 parts) and polyethyleneglycol (average molecular weight 4000) (30 parts) was vigorously stirred to obtain a uniform powdered form. This material was then charged into gelatine capsules using a conventional procedure such that each capsule contains 10, 20, 50 or 100 mg. of active ingredient suitable for oral administration for therapeutic purposes.

The active ingredient in the above procedure may be replaced by any other compound of formula I or a salt thereof mentioned herein.

EXAMPLE 3

A mixture of 1'-(3,4-dichlorobenzyl)-4-ethoxycarbonyl-spiro[pyrrolidine-3,3'-indoline]-2,2'5-trione(8.2 g.) and acetic acid (50 ml.) was heated under reflux for 22 hours. The solution obtained was cooled and poured into water (300 ml.). The solid which formed was collected by filtration and recrystallised from methanol to give 1'-(3,4-dichlorobenzyl)-spiro[pyrrolidine-3,3'-indoline]-2,2'5-trione (2.3 g.), m.p. 203°–204° C.

The starting material was obtained as follows:

A mixture of 1-(3,4-dichlorobenzyl)-indoline-2,3-dione (8.0 g.), ethyl cyanoacetate (2.95 g.) and piperidine (0.2 ml.) in ethanol (100 ml.) was heated under reflux for 4 hours. The mixture was then allowed to cool for 16 hours. The solid which had formed was collected by filtration and washed with methanol to give ethyl 2-[1-(3,4-dichlorobenzyl)-2-oxo-3-indolinidyl]-2-cyanoacetate (A) (6.5 g.), m.p. 140°–143° C.

Potassium cyanide (1.1 g.) was added to a solution of A (6.5 g.) in dimethyl sulphoxide (50 ml.) The mixture was stirred for 5 hours, diluted with water (60 ml.) and acidified to pH 5 with 2M hydrochloric acid. The resultant mixture was extracted with ether (3 × 100 ml.). The combined extracts were washed with water (2 × 50 ml.), dried (MgSO$_4$) and evaporated. The brown oil (containing ethyl 2-[1-(3,4-dichlorobenzyl)-3-cyano-2-oxo-3-indolinyl]-2-cyanoacetate) (7.3 g.) obtained was dissolved in methanol (100 ml.) and the resultant solution was saturated with hydrogen chloride gas at 0°–5° C., then left at ambient temperature for 2 days and finally heated under reflux for 4 hours. The solution was cooled and a small quantity of solid was removed by filtration. The filtrate was diluted with water (200 ml.) and the solid which formed was collected by filtration to give 1'-(3,4-dichlorobenzyl)-4-ethoxycarbonyl-spiro[pyrrolidine-3,3'-indoline]-2,2',5-trione (6.0 g.), m.p. 60°–85° C.

EXAMPLES 4 and 5

Using a similar procedure to that described in Example 3, there were obtained:

(Example 4): 1'-(4-methylbenzyl)-spiro[pyrrolidine3,3'-indoline]-2,2',5-trione, m.p. 218°–220° C. (EtOAc/petrol 60–80) in 94% yield, starting from 4-methoxycarbonyl-1'-(4-methylbenzyl)-spiro[pyrrolidine-3,3'-indoline]-2,2',5-trione (B); and (Example 5): 1'-(4-bromo-2-fluorobenzyl)-7'-methyl-spiro[pyrrolidine-3,3'-indoline]2,2',5-trione, m.p.

210°–211° C. (EtOAc/petrol 60–80) in 43% yield starting from 1'-(4-bromo-2-fluorobenzyl)-4-ethoxycarbonyl-7'-methyl-spiro[pyrrolidine-3,3'-indoline]-2,2',5-trione (C).

The initially formed intermediate spiro[pyrrolidine-3,3'-indoline]-2,2',5-trione-4-carboxylic acid of formula II was decarboxylated during the reaction.

The starting materials were obtained in a similar manner to A in Example 3:

B, was obtained as a solid, m.p. 160°–162° C. (EtOAc/petrol 60–80) and was itself obtained from ethyl 2-[3-cyano-7-methyl-1-(4-methylbenzyl)-2-oxo-3-indolinyl]-2-cyanoacetate, m.p. 128°–130° C. (EtoAc/petrol 60–80); in turn obtained by addition of cyanide to ethyl 2-[1-(4-methylbenzyl)-2-oxo-3-indolinidyl]-2-cyanoacetate, m.p. 143–145; itself formed by reaction of ethyl cyanoacetate with 1-(4-methylbenzyl)indoline-2,3-dione.

C, was obtained as a solid of satisfactory purity by TLC (SiO$_2$:EtOAc/petrol 60–80) and was itself obtained from ethyl 2-[1-(4-bromo-2-fluorobenzyl)-3-cyano-7-methyl- 2-oxo-3-indolinyl]-2-cyanoacetate, m.p. 130°–132° C. (EtOH); in turn obtained by addition of cyanide to ethyl 2-[1-(4-bromo-2-fluorobenzyl)-7-methyl-2-oxo-3-indolinidyl]-2-cyanoacetate, m.p. 159°–160° C.; itself formed by reaction of ethyl cyanoacetate with 1-(4-bromo-2-fluorobenzyl)-7-methylindoline-2,3-dione.

EXAMPLE 6

1'-(4-bromo-2-fluorobenzyl)-4-cyano-spiro[pyrrolidine-3,3'-indoline]-2,2',5-trione (1.0 g.) was heated under reflux in 48% w/w hydrogen bromide in acetic acid (30 ml.) for 90 minutes. The solution was poured into water (120 ml.). The precipitate was collected, washed with water (100 ml.), air dried and recrystallised twice from 2-propanol to give 1'-(4-bromo-2-fluorobenzyl)spiro[pyrrolidine-3,3'-indoline]-2,2',5-trione (0.25 g.), m.p. 218°–220° C.

The starting material was obtained as follows:

Potassium cyanide (5.85 g.) was added to a solution of ethyl 2-[1-(4-bromo 2-fluorobenzyl)-2-oxo3-indolinidyl]-2-cyanoacetate (D) (35.0 g.) in methanol (80 ml.). The mixture was stirred for 2 hours, cooled to 0° C. and then saturated with dry hydrogen chloride at 0°–10° C. The solution obtained was left overnight at ambient temperature, heated at 50°–55° C. for 1 hour and then under reflux for 4 hours. The cooled reaction solution deposited a solid which was collected; washed with water, air dried and then heated under reflux in acetic acid (85 ml.) for 12 hours. This mixture was cooled and the solid residue removed by filtration. The filtrate was evaporated, residual acetic acid being removed by azeotropic evaporation with toluene (3×150 ml.). The oily residue obtained was dissolved in ethyl acetate (100 ml.) and absorbed onto chromatographic silica gel (30 g.) by evaporation of the solvent. The residue was added to a column of silica gel (300 g.) made up in toluene. Elution with an increasing concentration of ethyl acetate in toluene (up to 25% v/v) and combination and evaporation of those fractions containing the major component (relative flow value 0.6), gave 1'-(4-bromo-2-flurobenzyl)-4-cyano-spiro[pyrrolidine3,3'-indoline]-2,2',5-trione (5.5 g.), m.p. 208°–210° C., after recrystallisation from ethyl acetate/petrol 60–80.

The starting material (D) was obtained as a red solid, m.p. 144°–147° C. by reaction of ethyl cyanoacetate with 1-(4-bromo-2-fluorobenzyl)indoline-2,3-dione, using a similar procedure to that described for the corresponding starting material for A in Example 3.

EXAMPLE 7

Sulphuryl chloride (2.74 g.) was added to a stirred suspension of 1'-(3,4-dichlorobenzyl)-spiro[pyrrolidine-3,3'-indoline]-2,2',5-trione (3.0 g.) in acetic acid (50 ml.). The mixture was stirred at 60° C. for 5 hours, cooled to ambient temperature and then stirred at this temperature for 16 hours. The mixture was then poured into water (250 ml.). The white solid which formed was collected by filtration, washed with water, air dried and recrystallised from 2-propanol to give 5'-chloro-1'-(3,4-dichlorobenzyl)spiro[pyrrolidine-3,3'-indoline]-2,2',5-trione (1.9 g.), m.p. 268°–270° C.

EXAMPLE 8

Sodium hydride (0.192 g., 50% w/w oil dispersion) was added to a stirred solution of 1'-(3,4-dichlorobenzyl)-spiro[pyrrolidine-3,3'-indoline]-2,2',5-trione (1.5 g.) in dry N,N-dimethylformamide (DMF) (20 ml.) under a nitrogen atmosphere. The solution was stirred for 30 minutes and then chloromethyl pivaloate (0.60 g.) was added. The mixture was stirred for 20 hours and then poured into water (30 ml.) The mixture obtained was extracted with ethyl acetate (2×40 ml.). The combined extracts were washed with water (2×15 ml.) dried (MgSO$_4$) and evaporated. The residue was dissolved in ethyl acetate (20 ml.). Chromatographic silica gel (10 g.) was added to the solution and then the solvent was evaporated. The residue was added to a column of silica gel (400 g.) made up in ethyl acetate/petrol (60–80 (1:1 v/v). This solvent mixture was used to elute the column. Evaporation of those combined fractions of eluate containing the major component [relative flow value 0.6, as judged by TLC (SiO$_2$: 50% v/v EtOAc/toluene)]gave 1'-(3,4-dichlorobenzyl)-3-pivaloyloxymethyl-spiro[pyrrolidine-3,3'-indoline]-2,2',5-trione as an oil which solidified slowly to give a solid (0.55 g.), m.p. 134°–135° C. (cyclohexane).

EXAMPLE 9

A solution of ethyl 2-[1-(3,4-dichlorobenzyl)-3-cyano-5-fluoro-2-oxo-3-indolinyl]-2-cyanoacetate (E) (2.0 g.) in 48% w/v hydrogen bromide in acetic acid (25 ml.) was heated under reflux for 3 hours. The solution was evaporated to half volume and poured into water (20 ml.). The mixture was extracted with ethyl acetate (2×50 ml.). The combined extracts were washed with water (2×50 ml.), brine (50 ml.), dried (MgSO$_4$) and evaporated. The residual solid was recrystallised from 2-propanol/petrol 60–80 to give 1'-(3,4-dichlorobenzyl)-5'-fluoro-spiro[pyrrolidine 3,3'-indoline]-2,2',5-trione (0.49 g.), m.p. 253°–254° C.

The starting material (E) was obtained as a solid, m.p. 134°–137° C., from ethyl 2-[1-(3,4-dichlorobenzyl)-5-fluoro-2-oxo-3-indolinidyl]-2-cyanoacetate (F) using an analogous procedure to that described in Example 3 for the equivalent starting material for A. The starting material (F) was similarly obtained as a solid, m.p. 144°–146° C. by reaction of ethyl cyanoacetate with 1-(3,4-dichlorobenzyl)-5-fluoroindoline-2,3-dione, using the procedure described for the equivalent starting material in Example 3.

EXAMPLE 10

Sodium hydride (1.1 g.; 23 mM; 50% w/w oil dispersion) was added to a stirred solution of spiro [pyrrolidine-3,3'-indoline]-2,2',5-trione (2.1 g.; 9.7 mM) in DMF (40 ml.), under an atmosphere of nitrogen. The mixture was stirred until effervescence had ceased and then heated to approximately 90° C. 3,4-Dichlorobenzyl chloride (2.2 g., 11.2 mM) was added dropwise. The reaction mixture was then allowed to cool to ambient temperature, stirred for 16 hours, and poured into water. The aqueous mixture was acidified (concentrated hydrochloric acid) and extracted with ethyl acetate (2×150 ml.). The combined extracts were washed with water (3×150 ml.), brine (150 ml.), dried $MgSO_4$) and evaporated. The residual oil was purified by chromatography on silica gel (150 g.) using an increasing gradient of ethyl acetate in toluene as eluant. Fractions were monitored by TLC ($SiO_2$: 50% v/v EtOAc/toluene) and those containing the major component (relative flow value : 0.5) were evaporated to give 1'-(3,4-dichlorobenzyl)-spiro[pyrrolidine-3,3'-indoline]-2,2',5-trione (0.6 g , m.p. 205°–207° C. (recrystallised twice from MeOH).

EXAMPLE 11

Ethanolic potassium hydroxide (12 ml., 1M) was added to a stirred solution of spiro[pyrrolidine-3,3'-indoline]-2,2',5-trione (1.0 g.) in dimethyl sulphoxide (10 ml.). 4-Bromobenzyl bromide (1.4 g.) was then added to the clear solution which was stirred for 4 hours. This solution was then added to water (100 ml.). The mixture was acidified (concentrated hydrochloric acid). The precipitate was collected, washed with water, air-dried and recrystallised from ethyl acetate/petrol 60–80 to give 1'-(4-bromobenzyl)spiro[pyrrolidine-3,3-indoline]-2,2',5-trione (0.15 g.) m.p. 218°–220° C.

EXAMPLES 12–21

Using a similar procedure to that described in Example 11, the following compounds of formula I were obtained in yields of 10–45% starting from the appropriate spiro[pyrrolidine-3,3'-indoline]-2,2',5trione of formula X (M=H) and alkylating agent of the formula Ra.Br:

| Example | Substituent on benzene ring A | Ra | m.p. (°C.) | recrystallisation Solvent(s) |
|---|---|---|---|---|
| 12 | — | 2-fluoro-4-iodobenzyl | 228–230 | i-Pr.OH |
| 13 | — | 4-chloro-2-fluorobenzyl | 203–205 | EtOAc/petrol 60–80 |
| 14 | — | hexyl | 110–112 | EtOAc/petrol 60–80 |
| 15 | — | cinnamyl | 188–190 | EtOAc/petrol 60–80 |
| 16 | — | 2-naphthyl-methyl | 212–213 | EtOAc/petrol 60–80 |
| 17 | 7'-fluoro | 2-fluoro-4-iodobenzyl | 241–243 | EtOAc/petrol 60–80 |
| 18 | — | 4-bromo-2-fluorobenzyl | 218–220 | EtOAc/petrol 60–80 |
| 19 | 5'-chloro | 4-bromo-2-fluorobenzyl | 222–224 | EtOAc/petrol 60–80 |
| 20 | — | butyl | 173–174 | MeOH |
| 21 | — | 3-trifluoromethylbenzyl | 131–133 | EtOAc/petrol 60–80 |

Notes
1. Aqueous potassium hydroxide was used as base in Ex. 12.
2. In general 2.0–2.5 molecular equivalents of base and 1.0–1.2 molecular equivalents of Ra.Br per molecular equivalent of X (M = H) were used.
3. The compounds in Examples 14–17, 19 and 21 were purified by chromatography using a similar procedure to that described in Example 10.

7'-Fluoro-spiro[pyrrolidine-3,3'-indoline]-2,2'-5-trione was obtained as a solid (m.p. 254°–256° C.) by cyclisation of ethyl 2-(3-cyano-7-fluoro-2-oxo-3-indolinyl)-2-cyanoacetate using hydrogen bromide in acetic acid as described in Example 9. The cyanoacetate was itself obtained as a brown oil from ethyl 2-(7-fluoro-2-oxo-3-indolinidyl)-2-cyanoacetate, itself obtained as a solid (m. p. 165°–166° C.) from 7-fluoroisatin and ethyl cyanoacetate, using the procedures described in Example 9. 7-Fluoroisatin was obtained as a solid (m.p. 190°–192° C.) by a conventional isatin synthesis starting from 2-fluoroaniline.

5'-Chloro-spiro[pyrrolidine-3,3'-indoline]-2,2', 5-trione was obtained as a solid (m.p. 295°–299° C.) by chlorination of the known spiro[pyrrolidine-3,3'-indoline]-2,2',5-trione [Arch. der Pharmazie, (Weinheim), 1970 303, 183–191]using sulphuryl chloride and an analogous procedure to that described in Example 7.

EXAMPLE 22

Using a similar procedure to that described in Example 11, but using sodium ethoxide as the base, ethanol as the solvent and 2,4-dichlorobenzyl chloride as the alkylating agent, there was obtained 1'-(2,4-dichlorobenzyl)-spiro[pyrrolidine-3,3'-indoline]-2,2', 5-trione, m.p. 231°–233° C. (EtOAc/petrol 60–80) in 20% yield.

EXAMPLES 23–42

Using a similar procedure to that described in Example 9, but using the appropriate ethyl 2-(1-substituted-3-cyano-2-oxo-3-indolinyl)-2-cyanoacetate of the formula IV (X=Y=CN, Z=$CO_2$Et), the following compounds of formula I were obtained:

| Example | Ra | Substituent on benzene ring A | m.p. (°C.) |
|---|---|---|---|
| 23 | hexyl | 7'-methyl | 96–98 |
| 24 | heptyl | 7'-methyl | 85–86 |
| 25 | 3-trifluoromethyl-benzyl | 7'-methyl | 226–228 |
| 26 | 3-trifluoromethyl-benzyl | 7'-fluoro | 196–198 |
| 27 | hexyl | 7'-fluoro | 96–97 |
| 28 | heptyl | 7'-fluoro | 72–73 |
| 29 | heptyl | 7'-trifluoromethyl | oil (Note 2) |
| 30 | 4-methylbenzyl | 7'-trifluoromethyl | 253–254 |
| 31 | pentyl | 7'-trifluoromethyl | oil (Note 3) |
| 32 | hexyl | 5'-fluoro | 114–115 |
| 33 | heptyl | 5'-fluoro | 105–106 |
| 34 | 4-methylbenzyl | 5'-fluoro | 134–135 |
| 35 | 3-trifluoromethyl-benzyl | 5'-fluoro | 173–174 |
| 36 | pentyl | 7'-fluoro | 118–119 |
| 37 | 3-trifluoromethyl-benzyl | 7'-chloro | 216–217 |
| 38 | 4-trifluoromethyl-benzyl | 7'-chloro | 208–209 |
| 39 | 4-methylbenzyl | 7'-chloro | 212–213 |
| 40 | 4-bromo-2-fluoro-benzyl | 7'-fluoro | 240–242 |
| 41 | 3,4-dichloro- | 7'-fluoro | 188–190 |

-continued

| Example | Ra | Substituent on benzene ring A | m.p. (°C.) |
|---|---|---|---|
| 42 | benzyl 3,4-dichloro-benzyl | 6'-chloro | 191–193 |

Notes
1. All the products were purified by column chromatography (medium pressure) on silica using a mixture of 10–25% v/v ethyl acetate in petrol 60–80 as eluant, and were then recrystallised (except Ex. 29 and 31) from ethyl acetate/petrol 60–80, and obtained in yields of 10–60%
2. NMR (90 MHz CDCl$_3$); δ 0.85 (3H, t, CH$_2$CH$_3$); 1.1–1.8 [10H, complex, (CH$_2$)$_5$]; 3.1 (2H, quartet, COCH$_2$N); 3.9 (2H, t, NCH$_2$); 6.9–7.7 (3H, complex, aromatic H); 9.5–10 (broad s, NH).
3. NMR (90 MHz, CDCl$_3$): δ 0.85 (3H, t, CH$_2$CH$_3$); 1.1–1.8 [6H, complex, (CH$_2$)$_3$]; 3.1 (2H, quartet, COCH$_2$N); 3.9 (2H, t, NCH$_2$); 6.9–7.7 (3H, complex, aromatic H); 8.0–9.2 (broad s, NH).

The necessary starting materials of formula IV were obtained as described in Example 9 and used without purification, starting from the corresponding dark red ethyl 2-(1-substituted-2-oxo-3-indolinidyl)-2-cyanoacetates of formula V (Y=CN, Z=CO$_2$Et) (shown in the following Table), which were themselves obtained as mixtures of geometric isomers in yields of 30–90%, using the procedure described in Examples 9 and 3:

| Compound No. | Ra | Substituent on benzene ring A | m.p. (°C.) |
|---|---|---|---|
| 1 | hexyl | 7-methyl | 56–58 (EtOH) |
| 2 | heptyl | 7-methyl | oil* |
| 3 | 3-trifluoromethyl-benzyl | 7-methyl | oil* |
| 4 | 3-trifluoromethyl-benzyl | 7-fluoro | oil* |
| 5 | hexyl | 7-fluoro | oil* |
| 6 | heptyl | 7-fluoro | oil* |
| 7 | heptyl | 7-trifluoromethyl | oil* |
| 8 | 4-methylbenzyl | 7-trifluoromethyl | oil* |
| 9 | pentyl | 7-trifluoromethyl | gum* |
| 10 | hexyl | 5-fluoro | 106–107 (EtOAc/petrol 60–80) |
| 11 | heptyl | 5-fluoro | 78–79 (EtOH) |
| 12 | 4-methylbenzyl | 5-fluoro | 192–194 (EtOH) |
| 13 | 3-trifluoromethyl-benzyl | 5-fluoro | 134–135 (EtOAc/petrol 60–80) |
| 14 | pentyl | 7-fluoro | oil* |
| 15 | 3-trifluoromethyl-benzyl | 7-chloro | 131–133 (EtOH) |
| 16 | 3-trifluoromethyl-benzyl | 7-chloro | oil* |
| 17 | 4-methylbenzyl | 7-chloro | oil* |
| 18 | 4-bromo-2-fluoro-benzyl | 7-fluoro | 128–130 (EtOH/Et$_2$O) |
| 19 | 3,4-dichlorobenzyl | 7-fluoro | 138–140 (EtOH/Et$_2$O) |
| 20 | 3,4-dichlorobenzyl | 6-chloro | 159–162 (EtOH/Et$_2$O) |

*Note: essentially pure by TLC (SiO$_2$: 25% EtOAC/petrol 60–80) showing 'E' and 'Z' geometric isomers as separate red spots.

The 1-substituted-indoline-2,3-diones of formula VI, used for the above and earlier Examples, were prepared by the following procedure, which is similar to that described by Schaefer [Archiv.Pharmazie (Weinheim), 1970, 303, 183–191]:

A solution of indoline-2,3-dione in DMF (10 ml. per gram of indoline-2,3-dione) was stirred with anhydrous potassium carbonate (1.5 molecular equivalents) for 20–30 minutes. The appropriate alkyl bromide or benzyl chloride or bromide (1.1 molecular equivalents) was then added and the mixture heated at 80°–85° C. for 1–2 hours, and then poured into an excess of ice-water (approximately 10x volume of DMF). The resultant orange solid was separated and air-dried to give the appropriate 1-substituted-indoline-2,3-dione.

Using this procedure, the following compounds of formula VI were obtained:

| Compound | Ra | Substituent on benzene ring A | m.p. (°C.) |
|---|---|---|---|
| a | hexyl | 7-methyl | 46–48 |
| b | heptyl | 7-methyl | 55–56 |
| c* | 3-trifluoromethyl-benzyl | 7-methyl | 169–171 |
| d* | 3-trifluoromethyl-benzyl | 7-fluoro | 108–109 (iPrOH) |
| e | hexyl | 7-fluoro | 99–100 |
| f | heptyl | 7-fluoro | 84–85 |
| g | heptyl | 7-trifluoromethyl | 43–44 |
| h | 4-methylbenzyl | 7-trifluoromethyl | |
| i | pentyl | 7-trifluoromethyl | 61–63 |
| j | hexyl | 5-fluoro | 53–54 (petrol 60–80) |
| k | heptyl | 5-fluoro | 67–68 |
| l | 4-methylbenzyl | 5-fluoro | 130–132 |
| m* | 3-trifluoromethyl-benzyl | 5-fluoro | 145–146 (iPrOH) |
| n | pentyl | 7-fluoro | 82–83 |
| o* | 3-trifluoromethyl-benzyl | 7-chloro | |
| p* | 4-trifluoromethyl-benzyl | 7-chloro | 160–161 |
| q | 4-methylbenzyl | 7-chloro | 185–187 |
| r | 4-bromo-2-fluoro-benzyl | 7-fluoro | 159–161 (EtOAc/petrol 60–80) |
| s | 3,4-dichlorobenzyl | 7-fluoro | 147–148 (EtOAc/petrol 60–80) |
| t* | 3,4-dichlorobenzyl | 6-chloro | 180–182 (i-PrOH) |
| u* | 3,4-dichlorobenzyl | none | 183–184 (EtOAc/petrol 60–80) |
| v* | 4-methylbenzyl | none | 141–143 (EtOAc/petrol 60–80) |
| w | 4-bromo-2-fluoro-benzyl | 7-methyl | 154–156 |
| x* | 3,4-dichlorobenzyl | 5-fluoro | 190–192 (EtOAc/petrol 60–80) |
| y | 4-bromo-2-fluoro-benzyl | none | 151–153 (i-PrOH/petrol 60–80) |

Note*:
These compounds were obtained using the appropriate benzyl chloride. The remaining compounds were obtained using the appropriate alkyl bromide or benzyl bromide.

EXAMPLE 43

1'-(3,4-Dichlorobenzyl)-spiro[pyrrolidine-3,3'-indoline]-2,2',5-trione (1.87 g.) was dissolved in water (50 ml.) containing sodium hydroxide (0.20 g.). Any residual solid was removed by filtration. The filtrate was evaporated, remaining traces of water being removed by azeotropic distillation with toluene. The residue was dried in vacuo (over P$_4$O$_{10}$). There was thus obtained the sodium salt of 1'-(3,4-dichlorobenzyl)-spiro[pyrrolidine-3,3'-indoline]-2,2',5-trione as an amorphous solid having a satisfactory microanalysis.

EXAMPLE 44

(All parts by weight)

An aqueous solution containing the sodium salt of 1'-(4-bromo-2-fluorobenzyl)-7'-methyl-spiro[pyrrolidine-3,3'-indoline-2,2',5-trione (10 parts), sodium bisulphite (as antoxidant, 3 parts) and phenyl mercuric acetate (as preservative, 0.02 parts) in water (1000 parts) was acidified with sufficient hydrochloric acid to bring the pH into the range 7.0–7.6. The solution was then sterile filtered in conventional manner in order to remove particulate contaminants. There is thus obtained a sterile solution containing approximately 1% of the active ingredient suitable for topical administration, for example to the eye, for medicinal purposes.

The active ingredient may be replaced by another compound of formula I or a salt thereof as described herein.

An ophthalmically acceptable buffer system, for example sodium borate/boric acid, may be included in the solution if desired.

Example 45

Using a similar procedure to that described in Example 1 or 2, but replacing the active ingredient by a biodegradable precursor of a compound of formula I as described herein, there may be made further compositions according to the invention suitable for oral administration for therapeutic purposes.

What is claimed is:

1. A pharmaceutical composition for inhibiting the enzyme aldose reductase comprising as active ingredient an effective amount of a 1'-substituted-spiro(pyrrolidine3,3'-indoline)-2,2',5-trione of the formula:

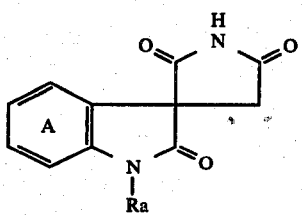

wherein Ra is benzyl bearing two independently selected halogeno substituents located at positions 2 and 4, or 3 and 4, or is benzyl bearing a bromo or trifluoromethyl substituent located at position 3 or 4; and benzene ring A is unsubstituted or bears one or two substituents independently selected from halogeno, (1-4C)alkyl, trifluoromethyl and nitro; or a salt thereof with a base affording a pharmaceutically acceptable cation; or the non-toxic, biodegradable 1-pivaloyloxymethyl precursor thereof; together with a pharmaceutically acceptable diluent or carrier.

2. A composition as claimed in claim 1 wherein, in the active ingredient, the halogeno substituents present as part of Ra are independently selected from fluoro, chloro, bromo or iodo substituents and the substituents which may be present on the benzene ring A are independently selected from fluoro, chloro, bromo, iodo, methyl, ethyl, trifluoromethyl and nitro substituents located at the 5', 6' or 7'-position.

3. A composition as claimed in claim 1 wherein, in the active ingredient, Ra is 3,4-dichlorobenzyl, 2-fluoro-4-iodobenzyl or 4-bromo-2-fluorobenzyl; and benzene ring A is unsubstituted or bears a fluoro, chloro, bromo methyl or trifluoromethyl substituent located in the 5', 6' or 7'-position.

4. A composition as claimed in claim 1 which is in a form suitable for oral, parenteral, rectal or topical ophthalmic administration.

5. A composition for oral administration as claimed in claim 4 which is in the form of a tablet, capsule, granule, dispersible powder, syrup, elixir, emulsion, suspension or gel.

6. A composition for topical ophthalmic administration as claimed in claim 4 which is in the form of an ointment, gel or sterile solution.

7. A method of inhibiting the enzyme aldose reductase in a warm-blooded animal requiring such treatment which comprises administering to said animal an aldose reductase inhibitory amount of a compound of formula I, according to claim 1, or a salt thereof with a base affording a pharmaceutically acceptable cation, or the non-toxic, biodegradable 1-pivaloyloxymethyl precursor thereof.

8. A composition according to claim 1 wherein the active ingredient is a compound selected from compounds where Ra and the benzene ring A are as follows:

| Ra | Benzene ring A substituent |
| --- | --- |
| 3,4-dichlorobenzyl | unsubstituted |
| 2-fluoro-4-iodobenzyl | unsubstituted |
| 4-bromo-2-fluorobenzyl | unsubstituted |
| 4-bromo-2-fluorobenzyl | 5'-chloro |
| 3,4-dichlorobenzyl | 5'-chloro |
| 3,4-dichlorobenzyl | 5'-fluoro |
| 3,4-dichlorobenzyl | 7'-fluoro |
| 4-bromo-2-fluorobenzyl | 7'-fluoro |
| 4-bromo-2-fluorobenzyl | 7'-methyl |
| 2-fluoro-4-iodobenzyl | 7'-fluoro |

9. A composition according to claim 8 wherein Ra is 4-bromo-2-fluorobenzyl and the benzene ring A has a 7' methyl substituent.

* * * * *